(12) United States Patent
Kuno et al.

(10) Patent No.: US 6,740,778 B2
(45) Date of Patent: May 25, 2004

(54) METHOD FOR THE PREPARATION OF OLEANOLIC ACID AND/OR MASLINIC ACID

(75) Inventors: Noriyasu Kuno, Yokosuka (JP); Gou Shinohara, Yokosuka (JP)

(73) Assignee: The Nisshin Oillio, Ltd., Tokyo (JP)

( * ) Notice: Subject to any disclaimer, the term of this patent is extended or adjusted under 35 U.S.C. 154(b) by 0 days.

(21) Appl. No.: 10/359,586

(22) Filed: Feb. 7, 2003

(65) Prior Publication Data

US 2003/0171613 A1 Sep. 11, 2003

Related U.S. Application Data

(63) Continuation of application No. PCT/JP01/02788, filed on Mar. 30, 2001.

(30) Foreign Application Priority Data

Aug. 8, 2000 (JP) ........................................ 2000-240347

(51) Int. Cl.$^7$ ........................... C07C 61/12; C07C 62/00
(52) U.S. Cl. ........................................ 562/508; 562/498
(58) Field of Search ................................. 562/508, 498

(56) References Cited

FOREIGN PATENT DOCUMENTS

| EP | 0 894 517 A1 | 2/1999 | |
|---|---|---|---|
| JP | 61-268648 | 11/1986 | |
| JP | 4-26650 | 1/1992 | |
| WO | 9804331 | * | 2/1998 |

* cited by examiner

*Primary Examiner*—Paul J. Killos
(74) *Attorney, Agent, or Firm*—Burns, Doane, Swecker & Mathis, L.L.P.

(57) ABSTRACT

The present invention relates to a method for preparing oleanolic acid and/or maslinic acid and physiologically acceptable salts thereof, which comprises the steps of extracting olive plant and/or products obtained in the olive oil-manufacturing processes with water and/or an organic solvent and then concentrating and/or fractionating/purifying the resulting extract.

26 Claims, No Drawings

METHOD FOR THE PREPARATION OF OLEANOLIC ACID AND/OR MASLINIC ACID

This application is a continuation of International Application No. PCT/JP01/02788 filed on Mar. 30, 2001, the entire content of which is hereby incorporated by reference.

This application claims priority under 35 U.S.C. §§ 119 and/or 365 to 2000-240347 filed in Japan on Aug. 8, 2000; the entire content of which is hereby incorporated by reference.

TECHNICAL FIELD

The present invention relates to a method for the preparation of oleanolic acid and/or maslinic acid as well as physiologically acceptable salts thereof and, in particular, to a method for the preparation of oleanolic acid and/or maslinic acid from olive plant (*Olea europaea* L.) and/or products derived from the olive oil-manufacturing processes.

BACKGROUND OF THE INVENTION

Olive is a plant belonging to genus olive of family Oleaceae, which has habitually been used as a raw material for foods. Olive is a plant widely cultivated for a long time and has presently and typically been grown on a large scale in the districts along the shore of the Mediterranean. Regarding the applications thereof, it is quite important and is not only used as oil stuffs such as olive oil in almost all the countries of the world including Japan and the United States, not to speak of the European countries, but also used as salt-preserved foods or materials for cosmetics and even as a herb (a medical plant). In addition, the olive oil cake has widely been used as a fertilizer, a feed and/or a fuel. In other words, it would be concluded that the olive is a vegetable material relatively stably available and highly safe for the human body.

Recently, the olive oil obtained through the oil expression of olive plant has been known as vegetable oil relatively hardly oxidized. Moreover, polyphenols present in the olive oil in trace amounts have attracted special interest and a variety of studies concerning, for instance, the physiological effects thereof have been conducted (see, for instance, International Olive Oil Council, New Food Industry, 1992, Vol.34, No. 4, pp. 28–52).

As another component of olive plant, it has been known that leaves of olive plant contain oleanolic acid and there have been elucidated, for instance, physiological effects thereof.

Oleanolic acid is a kind of oleanane type triterpenes and a compound present in, for instance, *Swertia japonica* Makino, *Eugenia caryophyllata* Thumb. (Clove), the rind of grapes and leaves of olive plant in its free state and in *Panax japonicus* C. A. Meyer, *Daucus carota* L. and *Beta vulgaris* L. in the form of saponin. Moreover, it may likewise be commercially available. There have conventionally been conducted a variety of studies concerning, for instance, physiological effects of oleanolic acid and it has been known that oleanolic acid possesses various effects such as a carcinogenic promoter-inhibitory effect (Japanese Un-Examined Patent Publication (hereunder referred to as "J.P. KOKAI") Sho 63-57519), an anti-inflammatory effect and an effect of promoting wound-healing (Japanese Examined Patent Publication (hereunder referred to as "J.P. KOKOKU") Hei 4-26623), an effect of inhibiting alcohol-absorption (J.P. KOKAI Hei 7-53385) and an effect of promoting new hair growing (J.P. KOKAI Hei 9-157139).

On the other hand, maslinic acid is a kind of oleanane type triterpenes and is a compound present in *Olea europaea* L. (olive), *Humulus lupulus* L. (hops), *Mentha arvensis* L. var. *piperascens* Holmes (Japanese mint), *Punica granatum* L., *Eugenia caryophyllata* Thumb. (Clove), *Salvia officinalis* L. (sage) and *Zizyphus vulgaris* Lam. Var. *inermis* Bunge, but it is not distributed so widely in the nature. Maslinic acid has been known to have an anti-inflammatory effect and anti-histamic effect.

As has been discussed above, oleanolic acid and maslinic acid are useful substances and therefore, it would be necessary to ensure the stable supply of these triterpenes. Regarding, in particular, maslinic acid, however, naturally occurring plant materials containing the same are deficient and there has not yet been established any effective method for preparing the same. Accordingly, a problem arises such that these compounds cannot stably be supplied and that they require high production coat.

Moreover, there has not yet been known any method for preparing either or both of oleanolic acid and maslinic acid from the same natural raw substances in highly purified states and any method for industrially mass-producing these substances in high efficiency.

DISCLOSURE OF THE INVENTION

Accordingly, it is an object of the present invention to provide a method for preparing oleanolic acid and/or maslinic acid and, in particular, to a method for industrially mass-producing these compounds from olive plant and/or products obtained from olive oil expression processes.

The inventors of this invention have conducted various investigations of methods for preparing oleanolic acid and/or maslinic acid and physiologically acceptable salts thereof starting from olive plant for achieving the foregoing object, have found a method for quite efficiently preparing these compounds and have thus completed the present invention.

The present invention thus relates to a method for preparing oleanolic acid and/or maslinic acid and physiologically acceptable salts thereof, which comprises the steps of extracting olive plant and/or products obtained in the olive oil-manufacturing processes with water and/or an organic solvent and then concentrating and/or conducting fractionation-purification treatment of, the resulting extract.

In this respect, oleanolic acid and maslinic acid as subjects of the present invention are substances represented by the following structural formulas (I) and (II), respectively. Moreover, the physiologically acceptable salts thereof are those derived from the —COOH groups in the structural formulas (I) and (II) and include those contained in olive plant and products obtained in the olive oil-manufacturing processes and those formed by treating oleanolic acid and/or maslinic acid prepared by the method of the present invention with basic mediums and/or basis substances. The kinds of salts are not restricted to specific ones inasmuch as they are currently used in, for instance, cosmetics or pharmaceutical composition and foods and beverages.

The present invention preferably relates to a method for preparing oleanolic acid and/or maslinic acid, which comprises the steps of extracting olive plant and/or products obtained in the olive oil-manufacturing processes with water and/or an organic solvent and then treating the resulting extracted substance and/or extracted liquid with an acidic medium and/or an acidic substance; and a method for preparing physiologically acceptable salts of oleanolic acid and/or maslinic acid, which comprises the steps of extracting olive plant and/or products obtained in the olive oil-manufacturing processes with water and/or an organic solvent and then treating the resulting extracted substance and/or extracted liquid with a basic medium and/or a basic substance.

According to preferred embodiments of the present invention, the olive plant preferably used in the foregoing method is at least one member selected from the group consisting of fruits, seeds, rinds, leaves, stems and buds or germs of olive and dried products, pulverized products and defatted products of these ingredients and the products obtained in the olive oil-manufacturing processes preferably used in the foregoing method are at least one member selected from the group consisting of strained lees, extraction residues, squeezed oil, extracted oil, degummed oil scum, deacidified oil scum, dark oil, waste decoloring agent, deodorized scum, oil-expressed juice, waste water and waste filter mediums.

The organic solvent used in the extraction step is a hydrophilic organic solvent, in particular, a water-containing hydrophihc organic solvent because of its industrial advantages such as good ability of penetrating into plant's tissues and achievement of high extraction efficiency. More specifically, the organic solvent is preferably at least one member selected from the group consisting of mixed solvents comprising chloroform and methanol and/or ethanol, pyridine, ethanol, dimethylsulfoxide and ethyl acetate, which are excellent in the solubilizing ability of oleanolic acid and/or maslinic acid, from the viewpoint of the extraction ability. Moreover, examples of hydrophilic organic solvents preferably used herein include at least one member selected from the group consisting of alcohols, mixtures of chloroform and alcohols, acetone, tetrahydrofuran, dimethyl-sulfoxide and pyridine.

A hydrophobic organic solvent may likewise be used as such an extraction solvent. Examples of such hydrophobic organic solvents preferably used herein include at least one member selected from the group consisting of ethyl acetate, hexane, diethyl ether and chloroform.

In addition, in view of the extraction efficiency, the temperature of water and/or the organic solvent used in the extraction is not less than 50° C. and preferably not less than 60° C. and the extraction treatment is preferably carried out under pressure.

Moreover, according to the preferred embodiments of the present invention, the concentration step is at least one treatment selected from the group consisting of soluble contents recovering treatment and/or insoluble contents recovering treatment, which make use of the solubility of the components present in the extract in water and/or organic solvents; liquid—liquid partition using water-hydrophobic organic solvent systems; recrystallization; re-precipitation; and a treatment, in which precipitates formed through cooling are recovered and the fractionation-purification treatment is preferably at least one member selected from the group consisting of recrystallization, re-precipitation, purification by normal phase and/or reversed phase chromatography, decolorization and deodorization.

According to a further aspect, the present invention relates to the foregoing method in which the total content of oleanolic acid, maslinic acid and physiologically acceptable salts thereof ranges from 85% to 100% and the purity of the resulting oleanolic acid and physiologically acceptable salts thereof is not less than 90% and the purity of the resulting maslinic acid and physiologically acceptable salts thereof is not less than 90%.

Structural Formula (I)

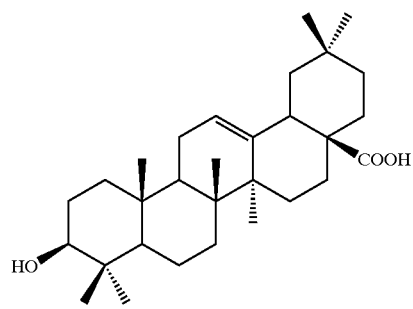

Structural Formula (II)

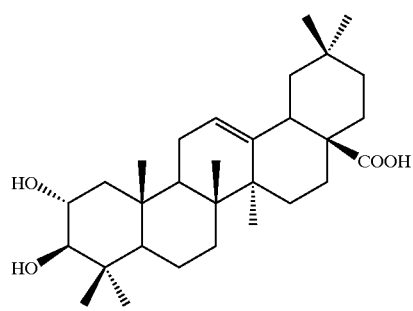

BEST MODE FOR CARRYING OUT THE INVENTION

The present invention relates to a method for preparing oleanolic acid and/or maslinic acid and physiologically acceptable salts thereof, which comprises the steps of extracting olive plant and/or products obtained in the olive oil-manufacturing processes with water and/or an organic solvent and then concentrating and/or fractionating/purifying the resulting extract.

In this respect, oleanolic acid and maslinic acid are substances represented by the following structural formulas (I) and (II), respectively. Moreover, the physiologically acceptable salts thereof are those derived from the —COOH groups in the structural formulas (I) and (II) and the kinds of salts are not restricted to specific ones inasmuch as they are currently used in, for instance, cosmetics or pharmaceutical composition and foods and beverages.

Oleanolic acid and/or maslinic acid and physiologically acceptable salts thereof can be obtained mainly from the fruits (including rinds), seeds and rinds of olive plant and they can likewise be obtained from leaves, stems and buds or germs thereof. It is also possible to suitably obtain these substances from dried, pulverized and defatted products thereof. Among these, preferred are defatted fruits (including rinds), and dried and pulverized products of rinds. Moreover, these compounds can likewise be obtained from products generated in the olive oil-manufacturing processes such as strained lees, extraction residues, squeezed (or compressed) oil, extracted oil, degummed oil scum, deacidified oil scum, dark oil, waste decoloring agent, deodorized scum, oil-expressed juice, waste water and waste filter mediums. Among them, preferred are strained lees and extraction residues.

The extraction process can be conducted using water and/or organic solvents. The extraction process may repeatedly be carried out, it may comprise a combination of different extraction methods or a combination of extraction treatments carried out using, for instance, different solvents. The extraction method and conditions therefor are not particularly restricted. For instance, the organic solvent usable herein may be either a hydrophilic organic solvent or a hydrophobic organic solvent, but preferably used herein are hydrophilic organic solvents from the viewpoint of industrial advantages such as good ability of penetrating into plant's tissues and achievement of high extraction efficiency. In the extraction process, it is particularly preferred to use a water-containing hydrophilic organic solvent. Moreover, in view of the solubility of, for instance, maslinic acid, the organic solvents may preferably be at least one member selected from the group consisting of mixed solvents comprising chloroform and methanol and/or ethanol, pyridine, ethanol, dimethylsulfoxide and ethyl acetate, since they are excellent in the ability of solubilizing oleanolic acid and/or maslinic acid. Moreover, examples of hydrophilic organic solvents preferably used herein include at least one member selected from the group consisting of alcohols, mixtures of chloroform and alcohols, acetone, tetrahydrofuran, dimethylsulfoxide and pyridine.

A hydrophobic organic solvent may likewise be used as such an extraction solvent. Examples of such hydrophobic organic solvents preferably used herein include at least one member selected from the group consisting of ethyl acetate, hexane, diethyl ether and chloroform.

In addition, in view of the extraction efficiency, the temperature of water and/or the organic solvent used in the extraction is not less than 50° C. and preferably not less than 60° C. since the solubility of the desired component is improved and plant's tissues get swollen and the extraction treatment is preferably carried out under pressure to thus promote the extraction of desired components.

In the present invention, the extracted substance (or product) and/or extracted liquid obtained through the foregoing extraction procedures can subsequently be subjected to a concentration treatment and/or fractionation-purification treatment to thus obtain highly purified oleanolic acid and/or maslinic acid as well as physiologically acceptable salts thereof. The concentration process can repeatedly be carried out or different concentration methods may be used in combination. Similarly, the fractionation-purification treatment may likewise repeatedly be carried out or different fractionation-purification treatments may be used in combination. Moreover, the fractionation-purification treatment may be conducted after the concentration treatment; or it may be carried out prior to the concentration treatment; or further the extract may continuously be subjected to a concentration treatment, a fractionation-purification treatment and a concentration treatment in this order. Combinations of these treatments other than those described above may of course be employed in the present invention.

Examples of such concentration step are soluble contents recovering treatments and/or insoluble contents recovering treatments, which make use of the solubility of the components present in the extract in water and/or organic solvents; liquid—liquid partition using water-hydrophobic organic solvent systems; recrystallization; re-precipitation; and a treatment, in which precipitates formed through cooling are recovered and examples of the fractionation-purification treatment are recrystallization, re-precipitation, purification by normal phase and/or reversed phase chromatography, decolorization and deodorization.

The combination of the foregoing extraction with the concentration treatment and/or the fractionation-purification treatment is not restricted to any particular one. For instance, olive plant is first extracted with water and/or a hydrophilic organic solvent, the hydrophilic organic solvent is partially or completely removed from the resulting extract, water is, if needed, added thereto, the resulting mixture is stirred and the fraction precipitated in the aqueous phase as insolubles is recovered to thus concentrate the extract. The water-insolubles thus precipitated may be recovered by, for instance, filtration or centrifugation, but the aqueous solution may be subjected to additional treatments such as addition of water and/or stirring in order to improve the rate of recovery. Alternatively, the extract evaporated to dryness obtained by removing the water and/or the hydrophilic organic solvent from the extract prepared from the olive plant may likewise be subjected to additional treatments such as addition of water and/or stirring and then the resulting insolubles are recovered through, for instance, filtration to thus concentrate the same. These concentrates can further be subjected to normal phase and/or reversed phase chromatography and/or fractionation-purification through recrystallization in order to obtain highly purified oleanolic acid and/or maslinic acid as well as physiologically acceptable salts thereof.

Moreover, the concentration of the extract by the liquid—liquid partition using a water-hydrophobic organic solvent system may be carried out by, for instance, removing the hydrophilic organic solvent from the extract obtained from the olive plant, adding, if needed, water to the remaining aqueous solution and then adding a hydrophobic organic solvent. Moreover, the extract evaporated to dryness may likewise be concentrated according to the liquid—liquid partition using a water-hydrophobic organic solvent system by adding water and then adding a hydrophobic organic solvent. These concentrates can further be subjected to normal phase and/or reversed phase chromatography and/or fractionation-purification through recrystallization in order to obtain highly purified oleanolic acid and/or maslinic acid as well as physiologically acceptable salts thereof.

The present invention preferably relates to the foregoing method in which the total content of oleanolic acid, maslinic acid and physiologically acceptable salts thereof ranges from 85% to 100% and in which the purity of the resulting oleanolic acid and physiologically acceptable salts thereof and the purity of the resulting maslinic acid and physiologically acceptable salts thereof are not less than 90%, preferably 90 to 100% and more preferably 95 to 100%.

The present invention also relates to a method for preparing oleanolic acid and/or maslinic acid comprising the steps of extracting olive plant and/or products obtained in the olive oil-manufacturing processes with water and/or an organic solvent and then treating the resulting extracted substance and/or extracted liquid with an acidic medium and/or an acidic substance. In other words, the present invention relates to a method for obtaining physiologically acceptable salts of oleanolic acid and/or maslinic acid in the form of their free states or as oleanolic acid and/or maslinic acid. The oleanolic acid and/or maslinic acid obtained in this method can likewise be subjected to a concentration and/or fractionation-purification treatments similar to those described above to obtain high purity oleanolic acid and/or maslinic acid.

The present invention further relates to a method for preparing physiologically acceptable salts of oleanolic acid and/or maslinic acid, which comprises the steps of extracting olive plant and/or products obtained in the olive oil-manufacturing processes with water and/or an organic solvent and then treating the resulting extracted substance and/or extracted liquid with a basic medium and/or a basic substance. In other words, the present invention relates to a method for obtaining oleanolic acid and/or maslinic acid in the form of physiologically acceptable salts thereof. The physiologically acceptable salts of oleanolic acid and/or maslinic acid obtained in this method can likewise be subjected to a concentration and/or fractionation-purification treatments similar to those described above to obtain high purity physiologically acceptable salts of oleanolic acid and/or maslinic acid.

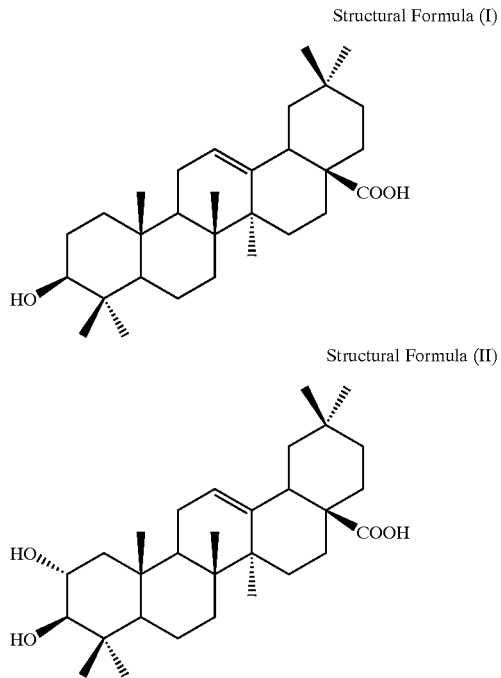

Structural Formula (I)

Structural Formula (II)

The oleanolic acid and maslinic acid as the subjects of the present invention are substances represented by the foregoing structural formulas (I) and (II), respectively.

Oleanolic acid is a kind of oleanane type triterpene and a compound present in, for instance, *Swertia japonica* Makino, *Eugenia caryophyllata* Thumb. (Clove), the rind of grapes and leaves of olive plant in its free state and in *Panax japonicus* C. A. Meyer, *Daucus carota* L. and *Beta vulgaris* L. in the form of saponin. Moreover, it may likewise be commercially easily available. There have conventionally been conducted a variety of studies concerning, for instance, physiological effects of oleanolic acid and it has been known that oleanolic acid possesses various effects such as a carcinogenic promoter-inhibitory effect (J.P. KOKAI Sho 63-57519), an anti-inflammatory effect and an effect of promoting wound-healing (J.P. KOKOKU Hei 4-26623), an effect of inhibiting alcohol-absorption (J.P KOKAI Hei 7-53385) and an effect of promoting new hair growing (J.P. KOKAI Hei 9-157139).

On the other hand, maslinic acid is a kind of oleanane type triterpene and is a compound present in *Olea europaea* L. (olive), *Humulus lupulus* L. (hops), *Mentha arvensis* L. var. *piperascens* Holmes (Japanese mint), *Punica granatum* L.., *Eugenia caryophyllata* Thumb. (Clove), *Salvia officinalis* L. (sage) and *Zizyphus vulgalis* Lam. Var. *inermis* Bunge. Maslinic acid has been known to have an anti-inflammatory effect and anti-histamic effect.

The term "physiologically acceptable salts" used herein means salts derived from the —COOH in the structural formula (i) and (II) and the salts are not restricted to specific ones inasmuch as they may be those currently used in cosmetics or pharmaceutical compositions and specific examples thereof include alkali metal salts such as sodium, potassium and lithium salts; alkaline earth metal salts such as calcium, magnesium, barium and zinc salts; alkylamine salts such as methylamine, dimethylamine, trimethylamine, ethylamine, diethylamine, triethylamine, propylamine, butylamine, tetrabutylamine, pentylamine and hexylamine salts; alkanolamine salts such as ethanolamine, diethanolamine, triethanolamine, propanolamine, dipropanolamine, isopropanolamine and diisopropanolamine salts; other organic amine salts such as piperazine and piperidine salts; and basic amino acid salts such as salts with lysine, alginine, histidine and tryptophane.

Oleanolic acid and/or maslinic acid and physiologically acceptable salts thereof can be obtained mainly from the fruits (including rinds) and seeds and they can likewise be obtained from leaves, stems and buds or germs thereof. It is also possible to suitably obtain these substances from dried, pulverized and defatted products of the foregoing raw materials.

Olive plant (*Olea europaea* L.) used as a raw material in the present invention may be any one irrespective of the growing district and the applications and examples thereof include home-grown olive plant and olive plant of European growth and those used for foods and for oil expression. The extract of the present invention can mainly be obtained from fruits or seeds of olive plant as well as the rinds, leaves, stems and buds or germs thereof. It is also possible to suitably obtain these substances from dried, pulverized and defatted products of the foregoing raw materials.

Moreover, the foregoing fruits of olive plant and defatted products thereof are preferably humidified by the addition of water or a steaming treatment. These fruits of olive plant and defatted products thereof get swollen to an appropriate degree according to the foregoing humidifying treatment and the extraction efficiency may be improved.

In particular, the use of such a defatted product of olive plant is preferred since the defatted product includes oleanolic acid and/or maslinic acid and physiologically acceptable salts thereof in high concentrations and it is not necessary to remove oil components from the resulting oleanolic acid and/or maslinic acid and physiologically acceptable salts thereof.

The defatted product as a raw material may be a squeezed and defatted product of olive or a defatted substance obtained through the extraction with, for instance, hexane.

Moreover, lipid components included in olive plant body or the defatted product thereof are removed through the extraction with at least one member selected from the group consisting of hydrocarbons such as pentane, hexane and heptane, lower fatty acid alkyl esters such as ethyl ester of acetic acid, and known non-aqueous organic solvents such as diethyl ether and the extraction treatment (or washing step) may, if necessary, be repeated to give a defatted product, which can likewise suitably be used in the present invention.

Thus, the oleanolic acid and/or maslinic acid and physiologically acceptable salts thereof according to the present invention may be prepared by extracting olive plant with water and/or an organic solvent.

In addition to the foregoing, the oleanolic acid and/or maslinic acid and physiologically acceptable salts thereof according to the present invention may likewise preferably obtained from products generated in the olive oil-manufacturing processes such as strained lees, extraction residues, squeezed oil, extracted oil, degummed oil scum, deacidified oil scum, dark oil, waste decoloring agent, deodorized scum, oil-expressed juice, waste water and waste filter mediums.

In other words, the present invention relates to a method for industrially and efficiently preparing oleanolic acid and/or maslinic acid and physiologically acceptable salts thereof from products generated in the olive oil-manufacturing processes.

The strained lees is obtained in compressing olive plant, in particular, fruits and/or seeds thereof and this is preferably used herein since it contains large amounts of oleanolic acid and/or maslinic acid and physiologically acceptable salts thereof, which are not eluted into the oil during the compression. In this connection, if the moisture content thereof is high, it is liable to be rotted and therefore, it is frequently dried. This strained lees has a high content of remaining oil components and is often used as a raw material for further oil expression. More specifically, the strained lees are extracted with lipophilic organic solvent such as hexane to give extracted oil and the extraction residues are thus produced in this oil expression process. The extracted oil is preferred in the present invention since it contains large amounts of oleanolic acid and/or maslinic acid and physiologically acceptable salts thereof as compared with the squeezed oil. Moreover, the use of extraction residues is preferred since the residues are not only contain a large quantity of oleanolic acid and/or maslinic acid and physiologically acceptable salts thereof, but also they have a low content of oil components and oleanolic acid and/or maslinic acid and physiologically acceptable salts thereof can thus highly efficiently be concentrated and/or purified.

As edible olive oil, particularly preferred are those free of any purification such as high quality squeezed oil products (also often referred to as extra virgin or virgin oil). On the other hand, low quality squeezed oil products (also often referred to as rampant-virgin) and extracted oil products (also often referred to as pomerse oil) have been used after purification and by-products are obtained in this purification (or refining) processes. Purification processes for oil include, for instance, degumming processes, deacidifying processes, decolorization processes and deodorizing processes and each process generates degumming oil cakes, de-acidifying oil cakes, waste decoloring agent and deodorizing scum as by-products.

The degumming is a process, which comprises the steps of adding a proper amount of water to oil, heating the resulting mixture with stirring to thus purifying the oil through the formation of a suspension containing gum components by the action of hydration, and then removing the suspended gum components using a centrifugal separator and degumming oil cakes are generated as by-products.

The de-acidifying is a process comprising the steps of heating, with stirring, degummed oil together with an alkaline aqueous solution such as an aqueous caustic soda solution to thus mainly convert free acids such as free fatty acids into salts (soap in case of fatty acids), removing the resulting salts and washing with water and this process is likewise accompanied by the formation of de-acidifying oil cakes as by-products. This de-acidifying process would permit the removal of about 90% of oleanolic acid and/or maslinic acid and physiologically acceptable salts thereof present in the oil and fats. More specifically, most of these components are partitioned off into the de-acidifying oil cakes and the use of the de-acidifying oil cakes as raw materials is preferred since they can efficiently provide oleanolic acid and/or maslinic acid and physiologically acceptable salts thereof.

The decoloring is a process comprising admixing a decoloring agent (such as China clay) with oil, which has been neutralized and washed with water after the deacidifying process, heating and stirring the resulting mixture under reduced pressure and then filtering the mixture to give good, pale colored and decolored oil and this process likewise generates waste decoloring agent containing oleanolic acid and/or maslinic acid and physiologically acceptable salts thereof adsorbed thereon.

The deodorization is a process comprising the steps of subjecting the decolored oil to a steam distillation step to thus remove any volatile components, which may give out bad smells, present in the oil and generates deodorization scum as a by-product. The use of the deodorization scum as a raw material is preferred since, in the deodorization process, not less than 50% of oleanolic acid and/or maslinic acid and physiologically acceptable salts thereof present in the oil prior to the deodorization treatment are partitioned off into the deodorization scum.

Among these, the de-acidifying oil cakes as by-products of the deacidifying process contain a large quantity of soap and they are also used as raw materials for fatty acids. After decomposing the soap component by the addition of sulfuric acid to the deacidifying oil cakes and then boiling the resulting mixture, the water present therein is separated to give dark oil containing a large quantity of free acids such as free fatty acids. This dark oil is preferably used as a raw material in the present invention since it is a product obtained by concentrating the deacidifying oil cakes having a high content of oleanolic acid and/or maslinic acid and physiologically acceptable salts thereof and therefore, the dark oil is further concentrated in the amount of oleanolic acid and/or maslinic acid.

Moreover, fruits of olive are crushed into a pasty product and then the resulting product is compressed to give an oil-expressed juice comprising a mixture of fruit juice and oil and compressed residues (or strained lees). In the process for obtaining compressed oil by processing this oil-expressed juice according to, for instance, centrifugation, waste water is simultaneously obtained, which comprises oil-insoluble components such as moisture.

The extraction process can be conducted using water and/or an organic solvent. The extraction treatment may repeatedly be carried out or may comprise a combination of different extraction methods or a combination of extraction treatments using different solvents or the like. The method and conditions for the extraction treatment are not particularly limited, but the present invention permits the preparation of oleanolic acid and/or maslinic acid and physiologically acceptable salts thereof through the extraction treatments with water, an organic solvent and/or a water-containing organic solvent.

Such an organic solvent usable in the extraction process may be either a hydrophilic organic solvent or a hydrophobic organic solvent. Preferably used herein are hydrophilic organic solvents since they are excellent from the industrial standpoint, for instance, they are excellent in the ability of penetrating into the plant's tissues and in the extraction efficiency and it is particularly preferred in the extraction treatment to use a water-containing organic solvent. This is because the moisture may get swollen the cell tissues to thus improve the extraction efficiency and accordingly, the water-containing organic solvent may ensure a high extraction efficiency and is preferred from such a standpoint. Such an organic solvent used for preparing oleanolic acid and/or maslinic acid and physiologically acceptable salts thereof according to the present invention from olive plant may be either a hydrophilic organic solvent or a hydrophobic organic solvent. Specific examples thereof include hydrophilic organic solvents, for instance, alcohols such as methyl alcohol, ethyl alcohol, glycerin, propylene glycol and 1,3-butylene glycol and other known organic solvents such as acetone, tetrahydrofuran, acetonitrile, 1,4-dioxane, pyridine, dimethylsulfoxide, N,N-dimethyl-formamide and acetic acid; and hydrophobic organic solvents, for instance, hexane, cyclohexane, carbon tetrachloride, chloroform, dichloromethane, 1,2-dichloroethane, diethyl ether, ethyl acetate, benzene and toluene. These organic solvents may be used alone or in any combination of at least two of them.

It is industrially preferred to use a hydrophilic organic solvent while taking into consideration, for instance, the ability of penetration into plant's tissues and the extraction efficiency. Specific examples of such preferred hydrophilic organic solvents are alcohols such as methyl alcohol, ethyl alcohol, glycerin, propylene glycol and 1,3-butylene glycol and other organic solvents such as acetone, tetrahydrofuran and acetonitrile, as well as these solvents, which contain water. The oleanolic acid and/or maslinic acid and physiologically acceptable salts thereof according to the present invention can be prepared from olive plant using at least one solvent selected from those listed above.

Moreover, preferably used herein are one or at least two members selected from the group consisting of mixed solvents comprising chloroform and methanol and/or ethanol, pyridine, ethanol, dimethylsulfoxide and ethyl acetate, while taking into consideration the solubility of oleanolic acid and/or maslinic acid. Hydrophilic organic solvents preferably used herein are at least one member selected from the group consisting of alcohols, chloroform-alcohol mixtures, acetone, tetrahydrofuran, dimethylsulfoxide and pyridine. These solvents are excellent in the ability of solubilizing oleanolic acid and/or maslinic acid and physiologically acceptable salts thereof and therefore, they permit the effective extraction of these components from, for instance, olive plant.

Hydrophobic organic solvents may likewise be used as extraction solvents. Such a hydrophobic organic solvent is preferably at least one member selected from the group consisting of ethyl acetate, hexane, diethyl ether and chloroform.

The conditions for the extraction are not particularly restricted. For instance, the extraction temperature ranges from 5 to 95° C., preferably 10 to 90° C., more preferably 15 to 85° C. and the extraction may effectively be carried out even at ordinary temperature. The extraction efficiency is apt to increase in proportion to the extraction temperature. The extraction may suitably be carried out at ordinary pressure, under pressure or under reduced pressure established by, for instance, aspiration. Moreover, the extraction may be conducted according to the shaking extraction technique or an extraction technique, which makes use of an extraction machine equipped with a stirring machine, for the improvement of the extraction efficiency. The extraction time may vary depending on other extraction conditions, but in general ranges from several minutes to several hours. In this respect, the longer the extraction time, the higher the degree of extraction. However, the extraction time may appropriately be determined in the light of other production conditions such as productive facilities and yield.

Moreover, in either of cases in which the solvent used in the extraction comprises water alone, an organic solvent alone or a mixture of water and an organic solvent, the solvent may be used in an amount ranging from 1 to 100 times and preferably 1 to 20 times (mass/mass, those in the following description are shown in the same way also) with respect to the amount of the raw material.

Moreover, the temperature of water and/or an organic solvent is not less than 50° C., preferably 50 to 100° C. and more preferably 60 to 100° C., likewise from the viewpoint of the extraction efficiency. More specifically, the use of such a solvent is preferred since it would permit the improvement of the solubility of the components to be extracted and the swelling of the plant's cells to thus improve the extraction efficiency. The extraction under heating conditions permits the achievement of an extraction efficiency on the order of 1.5 to 2.5 times that achieved by the extraction at ordinary temperature (about 20° C.).

The extraction may be carried out at a pressure preferably ranging from $0.5 \times 10^5$ to $10 \times 10^5$ Pa, more preferably $0.5 \times 10^5$ to $5 \times 10^5$ Pa, further preferably $0.5 \times 10^5$ to $3 \times 10^5$ Pa and most preferably $0.5 \times 10^5$ to $1.5 \times 10^5$ Pa, but more efficient extraction may be ensured when the extraction is carried out under pressure, for instance, ranging from $1 \times 10^5$ to $10 \times 10^5$ Pa, preferably $1 \times 10^5$ to $5 \times 10^5$ Pa, further preferably $1 \times 10^5$ to $3 \times 10^5$ Pa and most preferably $1 \times 10^5$ to $1.5 \times 10^5$ Pa, from the viewpoint of the extraction efficiency. Moreover, the extraction is preferably carried out at a pressure ranging from $1 \times 10^5$ to $1.5 \times 10^5$ Pa near the ordinary pressure, from the viewpoint of safety.

Further, the extraction is preferably conducted using a water-containing lower alcohol having a lower alcohol content of not more than 10% by mass, while taking into consideration, for instance, the yields of oleanolic acid and/or maslinic acid and physiologically acceptable salts thereof. It is further preferred to use a water-containing lower alcohol having a lower alcohol content ranging from 10 to 95% by mass and it is most preferred to use a water-containing lower alcohol whose lower alcohol content is adjusted to the range of from 30 to 95% by mass.

In this respect, examples of alcohols used in the present invention include known alcoholic solvents, for instance, primary alcohols such as methyl alcohol, ethyl alcohol, 1-propanol and 1-butanol; secondary alcohols such as 2-propanol and 2-butanol; tertiary alcohols such as 2-methyl-2-propanol; and liquid polyhydric alcohols such as ethylene glycol, propylene glycol and 1,3-butylene glycol. These solvents may be used alone or in any combination of at least two of them.

The term "lower alcohol" herein used means known alcohols having 1 to 4 carbon atoms, for instance, primary, secondary, tertiary and liquid polyhydric alcohols such as those listed above and these lower alcohols may be used alone or in any combination of at least two of them.

The solvents and moisture can be removed from the extracted product and/or extracted liquid thus obtained to obtain oleanolic acid and/or maslinic acid and physiologically acceptable salts thereof according to the present invention.

The removal of the solvents and/or moisture can be conducted by any known method such as distillation under reduced pressure, drying in vacuo (or under reduced pressure), freeze-drying (or lyophilization) and spray drying techniques. The oleanolic acid and/or maslinic acid and physiologically acceptable salts thereof according to the present invention may be in any state and they are of course be in a liquid or solution state containing solvents and/or moisture.

The extract derived from a defatted product is preferred in the present invention since it is free of any oil-soluble component such as triglycerides, sterols and tocopherols and it is not necessary to remove these components for purification. Moreover, the defatted product includes residues after the oil expression and the compression residues and extraction residues obtained after carrying out the oil expression for preparing olive oil may be used as such defatted products. Therefore, the use of the defatted product would permit the effective use of olive as a natural resource. These materials are usually disposed or used as feeds and therefore, this method is also excellent in the production cost.

In the present invention, the extracted product and/or extracted liquid obtained through the extraction treatment can then be subjected to a concentration treatment and/or fractionation-purification treatment to obtain high purity oleanolic acid and/or maslinic acid and physiologically acceptable salts thereof.

The concentration treatment can repeatedly be carried out or may comprise a combination of different concentration treatments. Similarly, the fractionation-purification treatment may repeatedly be conducted or may comprise a combination of different fractionation-purification treatments. Moreover, the concentration treatment may be carried out prior to or after the fractionation-purification treatment, or the concentration treatment may be carried out prior to the fractionation-purification treatment and then the concentration treatment may again be carried out. It is a matter of course that combinations of these treatments other than those listed above can be adopted in the present invention.

The concentration treatments are not restricted to specific ones inasmuch as they can improve the purity of the resulting oleanolic acid and/or maslinic acid and physiologically acceptable salts and specific examples thereof are soluble contents recovering treatments and/or insoluble contents recovering treatments, which make use of the solubility of the components present in the extract in water and/or organic solvents; liquid—liquid partition using water-hydrophobic organic solvent systems; recrystallization; re-precipitation; and a treatment, in which precipitates formed through cooling are recovered, which may be used alone or in any combination of at least two of them for conducting effective concentration.

Conditions for concentrating oleanolic acid and/or maslinic acid and physiologically acceptable salts are not restricted to specific ones. For instance, there may be listed a method, which makes use of the solubility in water. Oleanolic acid and/or maslinic acid and physiologically acceptable salts thereof according to the present invention have relatively low polarities and accordingly, they are compounds hardly soluble or insoluble in water. Thus, the extract from olive plant and/or products obtained in the olive oil-manufacturing processes can considerably be concentrated by separating the extract into components hardly soluble in water and/or those insoluble in water or components hardly soluble or insoluble in water and components easily soluble in water, while making the most use of the aforementioned characteristics.

The components hardly soluble or insoluble in water can easily be obtained by pouring the extract from olive plant into water, stirring the resulting mixture and then recovering the precipitates thus formed through, for instance, filtration.

Moreover, oleanolic acid and/or maslinic acid and physiologically acceptable salts thereof according to the present invention may, if needed, be concentrated through the liquid—liquid partition technique using a commonly used combination of solvents. It would be difficult to unconditionally determine such a combination of solvents, but examples thereof include those comprising hydrophobic organic solvents and examples of such hydrophobic organic solvents are known organic solvent such as hexane, carbon tetrachloride, chloroform, dichloromethane, 1,2-dichloroethane, diethyl ether, ethyl acetate, n-butanol, benzene and toluene. Among these, preferred are n-butanol, ethyl acetate and chloroform.

Oleanolic acid and/or maslinic acid and physiologically acceptable salts thereof are hardly soluble in water and therefore, undesirable water-soluble components of the extract can be removed by separating the aqueous phase from the hydrophobic organic solvent phase. Therefore, the hydrophobic organic solvent can be removed from the hydrophobic organic solvent phase to thus concentrate oleanolic acid and/or maslinic acid and physiologically acceptable salts thereof.

The fractionation-purification treatments usable herein are not restricted to specific ones inasmuch as they can improve the purity of oleanolic acid and/or maslinic acid and physiologically acceptable salts thereof and remove impurities, but examples of such fractionation-purification treatments particularly preferred are purification by normal phase and/or reversed phase chromatography, recrystallization, re-precipitation, decoloration and deodorization, which may be used alone or in any combination of at least two of them for the effective fractionation-purification.

Alternatively, oleanolic acid and/or maslinic acid and physiologically acceptable salts thereof according to the present invention can be fractionated and/or purified according to the normal phase and/or reversed phase chromatography. Among these, the use of the normal phase and/or reversed phase chromatography is particularly preferred for the fractionation-purification of the foregoing substances. Among the chromatography techniques, preferred are methods, which make use of liquid chromatography, since they would permit the fractionation-purification of oleanolic acid and/or maslinic acid and physiologically acceptable salts thereof according to the present invention in a high yield without causing any decomposition of these compounds. Specific examples of liquid chromatography techniques include normal phase liquid chromatography, reversed phase liquid chromatography, thin layer chromatography, paper chromatography and high performance liquid chromatography (HPLC) techniques and either of these liquid chromatography techniques may be used for the fractionation-purification of oleanolic acid and/or maslinic acid and physiologically acceptable salts thereof according to the present invention. Preferred are normal phase liquid chromatography, reversed phase liquid chromatography and high performance liquid chromatography (HPLC) techniques among others, while taking into consideration the resolution, throughput and the number of steps required. The fractionation-purification treatment permits the further concentration of the product obtained after the concentration and the isolation of the target component.

In this respect, the "normal phase liquid chromatography" herein used is, for instance, the following method. In other words, this method comprises the steps of preparing a column in which the fixed phase comprises, for instance, silica gel and the mobile phase comprises, for instance, a hexane-ethyl acetate mixed liquid or a chloroform-methanol mixed liquid; supplying the extracted product and/or extracted liquid derived from olive plant at a rate of loading ranging from 0.1% to 5% (wt (mass)/v (volume)); and then eluting a desired fraction according to a continuous elution method using a single mobile phase or the stepwise elution method in which the polarity of the solvent is gradually increased.

The "reversed phase liquid chromatography" herein used is, for instance, the following method. In other words, this method comprises the steps of preparing a column in which the fixed phase comprises, for instance, silica coupled with octadecyl silane (ODS) and the mobile phase comprises, for instance, a water-methanol mixed liquid, a water-acetonitrile mixed liquid or a water-acetone mixed liquid; supplying the extracted product and/or extracted liquid derived from olive plant at a rate of loading ranging from 0.1% to 5% (wt (mass)/v (volume)); and then eluting a desired fraction according to a continuous elution method using a single mobile phase or the stepwise elution method in which the polarity of the solvent is gradually increased.

The "high performance liquid chromatography (HPLC)" herein used is, in principle, similar to the foregoing normal phase liquid chromatography or the reversed phase liquid chromatography and is a technique for more rapidly carrying out the fractionation-purification at a higher resolution.

The foregoing techniques are preferably used alone or in any combination of at least two of them in the present invention since the use thereof permits the preparation of oleanolic acid and/or maslinic acid and physiologically acceptable salts thereof in a considerably concentrated and substantially impurity-free condition.

Moreover, the purity of oleanolic acid and/or maslinic acid and physiologically acceptable salts thereof can be adjusted by the use of the foregoing technique or appropriately combining at least two of them.

For instance, the method for effectively obtaining oleanolic acid and/or maslinic acid and physiologically acceptable salts thereof according to the present invention from olive plant comprises the steps of extraction with, for instance, a solvent such as water, a hydrophilic organic solvent, a water-containing hydrophilic organic solvent or other organic solvent; concentration, which makes use of the solubility in water; and purification by, for instance, using a column.

In addition, when a product obtained by concentrating the extract derived from olive plant with respect to oleanolic acid and/or maslinic acid and physiologically acceptable salts thereof according to the present invention and further subjecting the resulting concentrate to a fractionation-purification treatment is subsequently subjected to decoloration and/or deodorization treatments, undesirable components are removed, the resulting product is in a colorless to pale colored state and/or an odorless to almost odorless state. Therefore, the decoloration and/or deodorization treatments are preferably used in the present invention since the applications of the product are not restricted in color and/or perfume and it can be used in a wide variety of fields without any restriction.

Examples of such decolorizing methods include treatments with activated carbon and white clay and examples of deodorizing methods are likewise treatments with activated carbon and white clay and supercritical extraction and steam distillation.

The combination of the extraction treatment with the concentration treatment and/or the fractionation-purification treatment is not restricted to any specific one, but oleanolic acid and/or maslinic acid and physiologically acceptable salts can be obtained by combining the foregoing treatments.

Specific examples of the series of treatments are as follows, but the present invention is not restricted to any particular one.

For instance, after extracting olive plant with water and/or hydrophilic organic solvent, the hydrophilic organic solvent is partially or completely removed from the resulting extract, the extract is stirred while water is, if necessary, added thereto and then the insolubles in water, which are precipitated in the aqueous phase is recovered to thus concentrate the extract. The precipitated water-insoluble matter may be recovered by, for instance, filtration and centrifugation. In this respect, however, the aqueous solution is, if needed, subjected to various treatments such as addition of water and stirring for the improvement of the rate of recovery. Moreover, the extracted product, which is in a state evaporated to dryness and which is produced by removing the water and/or the hydrophilic organic solvent from the extract derived from olive plant may likewise be concentrated by subjecting, if necessary, the extracted product to various treatments such as addition of water and stirring and subsequent recovery of the resulting water insoluble matter by, for instance, filtration. This concentration method is preferred in the present invention since it is excellent in the safety as compared with the concentration method using solvents, the former method is carried out in an aqueous system and a wide variety of machinery and tools can be used therein. In addition, the method is preferred since the extract is almost free of any oil component and therefore, the method is excellent in the efficiency of concentration and/or purification.

These concentrates may be fractionated and purified by the normal phase and/or reversed phase liquid chromatography and/or recrystallization to thus give oleanolic acid and/or maslinic acid and physiologically acceptable salts thereof purified to a high purity.

Moreover, the extract derived from olive plant may be concentrated according to the liquid—liquid partition technique in which the hydrophilic organic solvent is removed from the extract, water is, if needed, added to the remaining aqueous solution and a hydrophobic organic solvent is further added thereto. Further, the extracted product, which is in the state evaporated to dryness, may likewise be concentrated according to the liquid—liquid partition technique in which water is, if needed, added to the extracted product and a hydrophobic organic solvent is further added thereto. These concentrates may be fractionated and purified by the normal phase and/or reversed phase liquid chromatography and/or recrystallization to thus give oleanolic acid and/or maslinic acid and physiologically acceptable salts thereof purified to a high purity.

In practicing the water-insoluble matter recovery method and the liquid—liquid partition method, the amount of water to be added is not specifically limited inasmuch as it permits the removal of the water-insoluble matter and the sufficient partition treatment, but the amount is preferably 1 to 100 times and more preferably 5 to 50 times and further preferably about 10 to 30 times the mass of the extract evaporated to dryness.

In addition, the amount of organic solvent to be added in the recovery of the organic solvent-soluble matter is not likewise particularly limited insofar as it permits the removal of the organic solvent-soluble matter and it preferably ranges from 1 to 100 times, more preferably 5 to 50 times and further preferably 10 to 30 times the mass of the extract evaporated to dryness. When using a water-organic solvent mixed solvent system, they are used in a volume ratio preferably ranging from 9:1 to 1:9 and more preferably 8:2 to 2:8.

In the liquid—liquid partition using water-hydrophobic organic solvent system, water and the hydrophobic organic solvent are preferably used in a volume ratio ranging from 9:1 to 1:9 and more preferably 8:2 to 2:8.

According to the production method of the present invention, the product containing oleanolic acid and/or maslinic acid and physiologically acceptable salts thereof may have a high overall purity of oleanolic acid and/or maslinic acid and physiologically acceptable salts on the order of 85 to 100%, preferably 90 to 100% and more preferably 95 to 100%.

Preferably, the present invention relates to the foregoing method in which the purity of the sum of oleanolic acid and physiologically acceptable salts thereof or that of the sum of maslinic acid and physiologically acceptable salts thereof are not less than 90%, preferably not less than 95% and more preferably not less than 99%.

The present invention further relates to a method for preparing oleanolic acid and/or maslinic acid, which comprises the steps of extracting olive plant and/or products obtained in the olive oil-manufacturing processes with water and/or an organic solvent and then treating the resulting extracted product and/or extracted liquid with an acidic medium and/or an acidic substance. In other words, this is a method for converting physiologically acceptable salts of oleanolic acid and/or maslinic acid into their free states or oleanolic acid and/or maslinic acid. The oleanolic acid and/or maslinic acid prepared according to this method can likewise be subjected to concentration and/or fractionation-purification treatments to thus give highly purified oleanolic acid and/or maslinic acid.

The treatment with an acidic medium and/or an acidic substance may be carried out after the extraction treatment and prior to the concentration or fractionation-purification treatment; or it may be carried out after the concentration and/or fractionation-purification treatments. The treatment with an acidic medium and/or an acidic substance may repeatedly be carried out over a plurality of times.

As such acidic mediums, there may be listed any acidic ion-exchange resin. The acidic substance may be any currently used acidic component capable of shifting the pH value to acid region and examples thereof include, but not limited to, a variety of acidic components, for instance, strong acids such as hydrochloric acid and sulfuric acid; carboxylic acids such as formic acid and acetic acid; sulfonic acids such as benzene-sulfonic acid, with strong acids being preferably used herein.

The amount of the acidic medium and/or acidic substance to be used may be such that, in either of cases, they can provide protons ($H^+$) in an amount of not less than the equivalent of the —COOH groups when the —COOH groups in the structural formulas (I) and (II) form salts. More specifically, the amount may vary depending on the differences in the quality of the acidic medium, the molecular weight of the acidic substance and the valency of acid used, but the amount of the acidic medium preferably ranges from 1 to 1000 times, more preferably 1 to 500 times the mass of the subject to be processed and that of the acidic substance preferably ranges from 0.05 to 5 times and more preferably 0.05 to 3 times the mass of the subject to be processed.

Further, the present invention relates to a method for preparing oleanolic acid and/or maslinic acid in the form of physiologically acceptable salts thereof, which comprises the steps of extracting olive plant and/or products obtained in the olive oil-manufacturing processes with water and/or an organic solvent and then treating the resulting extracted product and/or extracted liquid with a basic medium and/or a basic substance. More specifically, this is a method for converting oleanolic acid and/or maslinic acid into physiologically acceptable salts thereof. The physiologically acceptable salts of oleanolic acid and/or maslinic acid prepared according to this method can likewise be subjected to concentration and/or fractionation-purification treatments to thus give highly purified physiologically acceptable salts of oleanolic acid and/or maslinic acid.

The treatment with a basic medium and/or a basic substance may be carried out after the extraction treatment and prior to the concentration or fractionation-purification treatment; or it may be carried out after the concentration and/or fractionation-purification treatments. The treatment with a basic medium and/or a basic substance may repeatedly be carried out over a plurality of times.

As such basic mediums, there may be listed any basic ion-exchange resin. The basic substance may be any currently used basic component capable of shifting the pH value to basic region and examples thereof include, but not limited to, a variety of basic substances, for instance, strong bases such as sodium hydroxide; basic amino acids such as lysine and alginine; alkylamines such as ammonia and triethylamine; alkanolamines such as triethanolamine; and organic amines such as pyridine, with strong bases, basic amino acids, ammonia, alkylamines and alkanolamines being particularly preferred.

The amount of the basic medium and/or basic substance to be used may be such that, in either of cases, they can provide bases in an amount of not less than the equivalent of the —COOH groups present in the structural formulas (I) and (II). More specifically, the amount may vary depending on the differences in the molecular weights of the basic medium and/or the basic substance and the valency of acid used, but the amount of the basic medium preferably ranges from 1 to 1000 times, more preferably 1 to 500 times the mass of the subject to be processed and that of the basic substance preferably ranges from 0.05 to 5 times and more preferably 0.05 to 3 times the mass of the subject to be processed.

Physiologically acceptable salts of oleanolic acid and/or maslinic acid are converted into free acids or oleanolic acid and/or maslinic acid mainly for the purpose of making the product hardly soluble in water, while oleanolic acid and/or maslinic acid are converted into physiologically acceptable salts thereof mainly for the purpose of improving the water-solubility of the product.

The content of oleanolic acid, maslinic acid and physiologically acceptable salts thereof in the product may be determined by, for instance, the gas chromatography technique.

As has been discussed above in detail, the method of the present invention permits the preparation of highly purified oleanolic acid, maslinic acid and physiologically acceptable salts thereof.

Regarding the physiological effects of oleanolic acid and maslinic acid prepared according to the production method of the present invention, it has been known that oleanolic acid possesses a carcinogenic promoter-inhibitory effect, an anti-inflammatory effect, an effect of promoting wound-healing, an effect of inhibiting alcohol-absorption and an effect of promoting new hair growing and that maslinic acid possesses an anti-inflammatory effect and anti-histamic effect. Moreover, maslinic acid further possesses, for instance, a bleaching effect and an antitumor effect.

Oleanolic acid and maslinic acid having such effects may be used in a variety of fields and applications, for instance, oral and parenteral administration to human bodies, feeds for domestic animals and fishes, agricultural chemicals and industrial applications, but these substances are not particularly limited in, for instance, shapes.

Examples of preferred oral applications include the incorporation of these substances into foods and beverages and orally administered pharmaceutical agents. When these substances are used in foods and beverages and they are, for instance, incorporated into a diet, it would be expected to achieve an effect of, for instance, preventing any diseases caused by habitual way of life and therefore, they can be used as health foods and enriched or nutritional foods.

Moreover, the shapes or forms of these foods and beverages are not restricted to specific ones, but examples thereof include keepable foods, perishable foods, processed marine products, beverages, seasonings, edible fats and oils and dairy products.

Examples of particularly preferred parenteral applications include the incorporation of these substances into drugs externally applied to the skin. The shape of the drug externally applied to the skin is not particularly restricted and the substances may suitably be used in pharmaceutical agents, quasi-drugs and cosmetics. For instance, they are incorporated into pharmaceutical agents, they may be used as external preparations having effects of treating and/or alleviating a variety of skin diseases or disorders and further if they are used as cosmetics, they may be used as medicated cosmetics, which may possess bleaching effects.

EXAMPLES

The present invention will hereunder be described in more detail with reference to the following Examples and Comparative Examples. In these Examples, the term "%" means "% by mass". However, the present invention is not restricted to these specific Examples at all.

Preparation Example 1

To 1 kg of the compressed residue generated in the olive oil-manufacturing process and originated from Italy, there was added 10 volumes of hexane and extraction was continued at 20° C. and $1.02 \times 10^5$ Pa for 3 hours while vigorously stirring the extraction system. After passing the whole extraction system through a filter, the resulting filtrate was concentrated to dryness to give 117 g of an extracted product. The content of oleanolic acid and salts thereof and maslinic acid and salts thereof was determined by the gas chromatography (GC).

The entire extracted product was treated by silica gel column chromatography using a column packed with 40 volumes of silica gel (4680 g). First, an eluent (3:1 hexane/ethyl acetate mixed solvent) was passed through the column in an amount of about 5 times (23.4 L) the volume of the silica gel packed in the column to remove various kinds of undesirable fractions. Subsequently, desired oleanolic acid was eluted by passing an eluent (3:1 hexane/ethyl acetate mixed solvent) through the column in an amount of about 5 times (23.4 L) the volume of the silica gel packed in the column to thus give an oleanolic acid-containing fraction.

Then miscellaneous undesirable components were eluted by passing an eluent (1:1 mixture of hexane and ethyl acetate) through the column in an amount of 2.5 times (11.7 L) the silica gel packed in the column. Then intended maslinic acid was eluted by passing an eluent (1:1 mixture of hexane and ethyl acetate) through the column in an amount of 10 times (46.8 L) the silica gel packed in the column to thus obtain a maslinic acid-containing fraction.

After removing the hexane and the ethyl acetate from these fractions, they were vacuum dried to give 0.63 g of an oleanolic acid fraction and 0.11 g of a maslinic acid fraction, respectively. These products were analyzed by, for instance, the NMR and MS spectroscopic measurements and as a result, it was found that parts of the oleanolic acid and maslinic acid included in these fractions were in the form of salts such as sodium and potassium salts and that the majority of the remaining portions were in their free acid forms. Moreover, the purities of these substances were determined by GC. The results thus obtained are summarized in the following Table 1.

Preparation Example 2

To 1 kg of the compressed residue generated in the olive oil-manufacturing process and originated from Italy, there was added 10 volumes of a water-containing ethanol having an ethanol content of 65% by mass and extraction was continued at 20° C. and $1.02 \times 10^5$ Pa for 3 hours while vigorously stirring the extraction system. After passing the whole extraction system through a filter, the resulting filtrate was concentrated to dryness to give 58.9 g of an extracted product. The content of oleanolic acid and salts thereof and maslinic acid and salts thereof was determined by the GC technique.

To the extracted product, there were added 3 L of n-butanol and 3 L of water, followed by stirring the resulting mixture for 10 minutes and separation of the system into the n-butanol phase and the aqueous phase. After removing the n-butanol from the n-butanol phase, the resulting residue was vacuum dried to give 46.2 g of a concentrate.

The entire concentrate was treated by silica gel column chromatography using a column packed with about 40 volumes of silica gel (1850 g). First, an eluent (3:1 hexane/ethyl acetate mixed solvent) was passed through the column in an amount of about 5 times (9.3 L) the volume of the silica gel packed in the column to remove various kinds of undesirable fractions. Subsequently, desired oleanolic acid was eluted by passing an eluent (3:1 hexane/ethyl acetate mixed solvent) through the column in an amount of about 5 times (9.3 L) the volume of the silica gel packed in the column to thus give a crude oleanolic acid-containing fraction. Then miscellaneous undesirable components were eluted by passing an eluent (1:1 mixture of hexane and ethyl acetate) through the column in an amount of 2.5 times (4.6 L) the silica gel packed in the column. Then intended maslinic acid was eluted by passing an eluent (1:1 mixture of hexane and ethyl acetate) through the column in an amount of 10 times (18.5 L) the silica gel packed in the column to thus obtain a crude maslinic acid-containing fraction.

After the hexane and ethyl acetate were removed from these fractions, the resulting residues were vacuum dried to give 1.6 g of a crude oleanolic acid-containing fraction and 5.3 g of a crude maslinic acid-containing fraction.

Moreover, the resulting crude oleanolic acid-containing fraction was purified by the ODS column chromatography using a column packed with about 30 volumes (48 g) of octadecyl silica gel. First, miscellaneous undesirable components were eluted by passing an eluent (9:1 methanol/water mixture) through the column in an amount of 5 times (240 mL) the volume of the packed silica gel. Then intended oleanolic acid was eluted by passing an eluent (9:1 methanol/water mixture) through the column in an amount of 10 times (480 mL) the volume of the packed silica gel to give a purified oleanolic acid fraction. After removal of the methanol from this fraction, the resulting residue was dried under reduced pressure to give 1.3 g of purified oleanolic acid.

Similarly, the resulting crude maslinic acid fraction was purified by the ODS column chromatography using a column packed with about 30 volumes (160 g) of octadecyl silica gel. First, miscellaneous undesirable components were eluted by passing an eluent (8:2 methanol/water mixture) through the column in an amount of 10 times (1.6 L) the volume of the packed silica gel. Then intended maslinic acid was eluted by passing an eluent (8:2 methanol/water mixture) through the column in an amount of 30 times (4.8 L) the volume of the packed silica gel to give a purified maslinic acid fraction. After removal of the methanol from this fraction, the resulting residue was dried under reduced pressure to give 4.1 g of purified maslinic acid.

These products were analyzed by, for instance, the NMR and MS spectroscopic measurements and as a result, it was found that parts of the oleanolic acid and maslinic acid included in these fractions were in the form of salts such as sodium and potassium salts and that the majority of the remaining portions were in their free acid forms. Moreover, the purities of these substances were determined by GC. The results thus obtained are summarized in the following Table 1.

Preparation Example 3

To 1 kg of the extraction residue generated in the olive oil-manufacturing process and originated from Italy, there was added 10 volumes of hexane and extraction was continued at 20° C. and $1.02 \times 10^5$ Pa for 3 hours while vigorously stirring the extraction system. After passing the whole extraction system through a filter, the resulting filtrate was concentrated to dryness to give 25 g of an extracted product. The content of oleanolic acid and salts thereof and maslinic acid and salts thereof was determined by the GC technique.

The entire extracted product was treated by silica gel column chromatography using a column packed with 40 volumes of silica gel (1000 g). First, an eluent (3:1 hexane/ethyl acetate mixed solvent) was passed through the column in an amount of about 5 times (5 L) the volume of the silica gel packed in the column to remove various kinds of undesirable fractions. Subsequently, desired oleanolic acid was eluted by passing an eluent (3:1 hexane/ethyl acetate mixed solvent) through the column in an amount of about 5 times (5 L) the volume of the silica gel packed in the column to thus give an oleanolic acid-containing fraction.

Then miscellaneous undesirable components were eluted by passing an eluent (1:1 mixture of hexane and ethyl acetate) through the column in an amount of 2.5 times (2.5 L) the silica gel packed in the column. Then intended maslinic acid was eluted by passing an eluent (1:1 mixture of hexane and ethyl acetate) through the column in an amount of 10 times (10 L) the silica gel packed in the column to thus obtain a maslinic acid-containing fraction.

After removing the hexane and the ethyl acetate from these fractions, they were vacuum dried to give 0.14 g of an oleanolic acid fraction and 0.02 g of a maslinic acid fraction, respectively.

These products were analyzed by, for instance, the NMR and MS spectroscopic measurements and as a result, it was found that parts of the oleanolic acid and maslinic acid included in these fractions were in the form of salts such as sodium and potassium salts and that the majority of the remaining portions were in their free acid forms. Moreover, the purities of these substances were determined by GC. The results thus obtained are summarized in the following Table 1.

Preparation Example 4

To 1 kg of the extraction residue generated in the olive oil-manufacturing process and originated from Italy, there was added 10 volumes of a water-containing ethanol having an ethanol content of 65% by mass and extraction was continued at 20° C. and $1.02 \times 10^5$ Pa for 3 hours while vigorously stirring the extraction system. After passing the whole extraction system through a filter, the resulting filtrate was concentrated to dryness to give 41.0 g of an extracted product. The content of oleanolic acid and salts thereof and maslinic acid and salts thereof was determined by the GC technique.

To the extracted product, there were added 2 L of n-butanol and 2 L of water, followed by stirring the resulting mixture for 10 minutes and separation of the system into the n-butanol phase and the aqueous phase. After removing the n-butanol from the n-butanol phase, the resulting residue was vacuum dried to give 27.0 g of a concentrate.

Then the concentrate was treated by silica gel column chromatography using a column packed with about 40 volumes of silica gel (1080 g). First, an eluent (3:1 hexane/ethyl acetate mixed solvent) was passed through the column in an amount of about 5 times (5.4 L) the volume of the silica gel packed in the column to remove various kinds of undesirable fractions. Subsequently, desired oleanolic acid was eluted by passing an eluent (3:1 hexane/ethyl acetate mixed solvent) through the column in an amount of about 5 times (5.4 L) the volume of the silica gel packed in the column to thus give a crude oleanolic acid-containing fraction. Then miscellaneous undesirable components were eluted by passing an eluent (1:1 mixture of hexane and ethyl acetate) through the column in an amount of 2.5 times (2.7 L) the silica gel packed in the column. Then intended maslinic acid was eluted by passing an eluent (1:1 mixture of hexane and ethyl acetate) through the column in an amount of 10 times (10.8 L) the silica gel packed in the column to thus obtain a crude maslinic acid-containing fraction.

After the hexane and ethyl acetate were removed from these fractions, the resulting residues were vacuum dried to give 1.6 g of a crude oleanolic acid-containing fraction and 5.8 g of a crude maslinic acid-containing fraction.

Moreover, the resulting crude oleanolic acid-containing fraction was purified by the ODS column chromatography using a column packed with about 30 volumes (48 g) of octadecyl silica gel. First, miscellaneous undesirable components were eluted by passing an eluent (9:1 methanol/water mixture) through the column in an amount of 5 times (240 mL) the volume of the packed silica gel. Then intended oleanolic acid was eluted by passing an eluent (9:1 methanol/water mixture) through the column in an amount of 10 times (480 mL) the volume of the packed silica gel to give a purified oleanolic acid fraction. After removal of the methanol from this fraction, the resulting residue was dried under reduced pressure to give 1.3 g of purified oleanolic acid.

Similarly, the resulting crude maslinic acid fraction was purified by the ODS column chromatography using a column packed with about 30 volumes (180 g) of octadecyl silica gel. First, miscellaneous undesirable components were eluted by passing an eluent (8:2 methanol/water mixture) through the column in an amount of 10 times (1.8 L) the volume of the packed silica gel. Then intended maslinic acid was eluted by passing an eluent (8:2 methanol/water mixture) through the column in an amount of 30 times (5.4 L) the volume of the packed silica gel to give a purified maslinic acid fraction. After removal of the methanol from this fraction, the resulting residue was dried under reduced pressure to give 4.5 g of purified maslinic acid.

These products were analyzed by, for instance, the NMR and MS spectroscopic measurements and as a result, it was found that parts of the oleanolic acid and maslinic acid included in these fractions were in the form of salts such as sodium and potassium salts and that the majority of the remaining portions were in their free acid forms. Moreover, the purities of these substances were determined by GC. The results thus obtained are summarized in the following Table 1.

Preparation Example 5

To an extracted product obtained by a method similar to that described in Example 4, there was added 780 g of water and the resulting mixture was vigorously stirred at 20° C. and $1.02 \times 10^5$ Pa for one hour. The whole mixture was treated by centrifugation, followed by removal of the supernatant through decantation and drying of the remaining precipitates to give 21.9 g of a concentrate.

Then the concentrate was treated by silica gel column chromatography using a column packed with about 40 volumes of silica gel (880 g). First, an eluent (3:1 hexane/ ethyl acetate mixed solvent) was passed through the column in an amount of about 5 times (4.4 L) the volume of the silica gel packed in the column to remove various kinds of undesirable fractions. Subsequently, desired oleanolic acid and maslinic acid were eluted by passing an eluent (1:1 hexane/ethyl acetate mixed solvent) through the column in an amount of about 15 times (13.2 L) the volume of the silica gel packed in the column to thus give a crude fraction containing a mixture of oleanolic acid and maslinic acid.

After the removal of the hexane and ethyl acetate from the fraction, the resulting residue was dried under reduced pressure to give 9.5 g of a crude fraction containing a mixture of oleanolic acid and maslinic acid.

Then the resulting crude fraction containing the oleanolic acid-maslinic acid mixture was purified by the recrystallization technique. In other words, a proper amount of ethyl acetate was added to the crude fraction, the mixture was heated to dissolve the fraction, cooled by allowing it to stand and the precipitates formed were recovered through filtration. The recrystallization procedure was repeated twice to give 6.2 g of a purified mixture of oleanolic acid and maslinic acid.

The product was analyzed by, for instance, the NMR and MS spectroscopic measurements and as a result, it was found that parts of the oleanolic acid and maslinic acid contained in the purified mixture were in the form of salts such as sodium and potassium salts and that the majority of the remaining portions were in their free acid forms. Moreover, the purities of these substances were determined by GC. The results thus obtained are summarized in the following Table 1.

Preparation Example 6

To 1 kg of the extraction residue generated in the olive oil-manufacturing process and originated from Italy, there was added 10 volumes of a water-containing ethanol having an ethanol content of 65% by mass and extraction was continued at 20° C. and $1.02 \times 10^5$ Pa for 3 hours while vigorously stirring the extraction system. The yield of the resulting extracted product was found to be 41 g. The content of oleanolic acid and salts thereof and maslinic acid and salts thereof present in the extracted product was determined by the GC technique. After the filtration of the whole extracted product, the ethanol was completely removed from the resulting filtrate to give the aqueous phase of the extracted product, water was added to the recovered aqueous phase to a total amount of 820 g for the improvement of the efficiency of recovering water-insoluble matter and the mixture was vigorously stirred at room temperature for one hour. After the whole solution was treated by centrifugation, the resulting supernatant was removed by decantation and the remaining precipitates were dried to give 21.9 g of a concentrate.

Then the concentrate was treated by silica gel column chromatography using a column packed with about 40 volumes of silica gel (880 g). First, an eluent (3:1 hexane/ ethyl acetate mixed solvent) was passed through the column in an amount of about 5 times (4.4 L) the volume of the silica gel packed in the column to remove various kinds of undesirable fractions. Subsequently, desired oleanolic acid was eluted by passing an eluent (3:1 hexane/ethyl acetate mixed solvent) through the column in an amount of about 5 times (4.4 L) the volume of the silica gel packed in the column to thus give a crude oleanolic acid-containing fraction. Then miscellaneous undesirable components were eluted by passing an eluent (1:1 mixture of hexane and ethyl acetate) through the column in an amount of 2.5 times (2.2 L) the silica gel packed in the column. Then intended maslinic acid was eluted by passing an eluent (1:1 mixture of hexane and ethyl acetate) through the column in an amount of 10 times (8.8 L) the silica gel packed in the column to thus obtain a crude maslinic acid-containing fraction.

After the hexane and ethyl acetate were removed from these fractions, the resulting residues were vacuum dried to give 1.6 g of a crude oleanolic acid-containing fraction and 5.8 g of a crude maslinic acid-containing fraction.

Moreover, the resulting crude oleanolic acid-containing fraction was purified by the ODS column chromatography using a column packed with about 30 volumes (48 g) of octadecyl silica gel. First, miscellaneous undesirable components were eluted by passing an eluent (9:1 methanol/ water mixture) through the column in an amount of 5 times (240 mL) the volume of the packed silica gel. Then intended oleanolic acid was eluted by passing an eluent (9:1 methanol/water mixture) through the column in an amount of 10 times (480 mL) the volume of the packed silica gel to give a purified oleanolic acid fraction. After the removal of the methanol from this fraction, the resulting residue was dried under reduced pressure to give 1.3 g of purified oleanolic acid.

Similarly, the resulting crude maslinic acid-containing fraction was purified by the ODS column chromatography using a column packed with about 30 volumes (180 g) of octadecyl silica gel. First, miscellaneous undesirable components were eluted by passing an eluent (8:2 methanol/ water mixture) through the column in an amount of 10 times (1.8 L) the volume of the packed silica gel. Then intended maslinic acid was eluted by passing an eluent (8:2 methanol/ water mixture) through the column in an amount of 30 times (5.4 L) the volume of the packed silica gel to give a purified maslinic acid fraction. After the removal of the methanol from this fraction, the resulting residue was dried under reduced pressure to give 4.5 g of purified maslinic acid.

Then the resulting purified oleanolic acid was further purified by recrystallization. More specifically, a proper amount of ethyl acetate was added to the purified oleanolic acid, the mixture was heated to dissolve the same, cooled by allowing it to stand and the precipitates formed were recovered through filtration to give 1.1 g of recrystallized oleanolic acid. The same recrystallization procedures used above were repeated using the purified maslinic acid to thus give 3.7 g of recrystallized maslinic acid.

These products were analyzed by, for instance, the NMR and MS spectroscopic measurements and as a result, it was found that parts of the oleanolic acid and maslinic acid included in these fractions were in the form of salts such as sodium and potassium salts and that the majority of the remaining portions were in their free acid forms. Moreover, the purities of these substances were determined by GC. The results thus obtained are summarized in the following Table 1.

Preparation Example 7

To 1 kg of the extraction residue generated in the olive oil-manufacturing process and originated from Italy, there was added 10 volumes of a water-containing ethanol having an ethanol content of 65% by mass and extraction was continued at 50° C. and $1.02 \times 10^5$ Pa for 3 hours while vigorously stirring the extraction system. The yield of the resulting extracted product was found to be 65.6 g. The content of oleanolic acid and salts thereof and maslinic acid and salts thereof present in the extracted product was determined by the GC technique. After the filtration of the whole extracted product, the ethanol was completely removed from the resulting filtrate to give the aqueous phase of the extracted product, water was added to the recovered aqueous phase to a total amount of 1310 g for the improvement of the efficiency of recovering water-insoluble matter and the mixture was vigorously stirred at room temperature for one hour. After the whole solution was treated by centrifugation, the resulting supernatant was removed by decantation and the remaining precipitates were dried to give 39.1 g of a concentrate.

Then the concentrate was treated by silica gel column chromatography using a column packed with about 40 volumes of silica gel (1570 g). First, an eluent (3:1 hexane/ethyl acetate mixed solvent) was passed through the column in an amount of about 5 times (7.9 L) the volume of the silica gel packed in the column to remove various kinds of undesirable fractions. Subsequently, desired oleanolic acid was eluted by passing an eluent (3:1 hexane/ethyl acetate mixed solvent) through the column in an amount of about 5 times (7.9 L) the volume of the silica gel packed in the column to thus give a crude oleanolic acid-containing fraction. Then miscellaneous undesirable components were eluted by passing an eluent (1:1 mixture of hexane and ethyl acetate) through the column in an amount of 2.5 times (3.9 L) the silica gel packed in the column. Then intended maslinic acid was eluted by passing an eluent (1:1 mixture of hexane and ethyl acetate) through the column in an amount of 10 times (15.7 L) the silica gel packed in the column to thus obtain a crude maslinic acid-containing fraction.

After the hexane and ethyl acetate were removed from these fractions, the resulting residues were vacuum dried to give 2.9 g of a crude oleanolic acid-containing fraction and 10.3 g of a crude maslinic acid-containing fraction.

Moreover, the resulting crude oleanolic acid-containing fraction was purified by the ODS column chromatography using a column packed with about 30 volumes (87 g) of octadecyl silica gel. First, miscellaneous undesirable components were eluted by passing an eluent (9:1 methanol/water mixture) through the column in an amount of 5 times (440 mL) the volume of the packed silica gel. Then intended oleanolic acid was eluted by passing an eluent (9:1 methanol/water mixture) through the column in an amount of 10 times (870 mL) the volume of the packed silica gel to give a purified oleanolic acid fraction. After the removal of the methanol from this fraction, the resulting residue was dried under reduced pressure to give 2.3 g of purified oleanolic acid.

Similarly, the resulting crude maslinic acid-containing fraction was purified by the ODS column chromatography using a column packed with about 30 volumes (310 g) of octadecyl silica gel. First, miscellaneous undesirable components were eluted by passing an eluent (8:2 methanol/water mixture) through the column in an amount of 10 times (3.1 L) the volume of the packed silica gel. Then intended maslinic acid was eluted by passing an eluent (8:2 methanol/water mixture) through the column in an amount of 30 times (9.3 L) the volume of the packed silica gel to give a purified maslinic acid fraction. After the removal of the methanol from this fraction, the resulting residue was dried under reduced pressure to give 8.0 g of purified maslinic acid.

Then the resulting purified oleanolic acid was further purified by recrystallization. More specifically, a proper amount of ethyl acetate was added to the purified oleanolic acid, the mixture was heated to dissolve the same, cooled by allowing it to stand and the precipitates formed were recovered through filtration to give 2.0 g of recrystallized oleanolic acid. The same recrystallization procedures used above were repeated using the purified maslinic acid to thus give 6.6 g of recrystallized maslinic acid.

These products were analyzed by, for instance, the NMR and MS spectroscopic measurements and as a result, it was found that parts of the oleanolic acid and maslinic acid included in these fractions were in the form of salts such as sodium and potassium salts and that the majority of the remaining portions were in their free acid forms. Moreover, the purities of these substances were determined by GC. The results thus obtained are summarized in the following Table 1.

TABLE 1

|  |  | Preparation Example No. | | |
| --- | --- | --- | --- | --- |
|  |  | 1 | 2 | 3 |
| Raw Material | | Compressed Residue | Compressed Residue | Extraction residue |
| Extraction Solvent | | Hexane | $H_2O$—EtOH[1] | Hexane |
| Extracted Product | Amt. of Extract (g) | 117 | 58.9 | 25 |
|  | Content of oleanolic acid | 0.50 (%) | 2.2 (%) | 0.52 (%) |
|  | Content of maslinic acid | 0.09 (%) | 7.0 (%) | 0.07 (%) |
| Concentration/fractionation-Purification | | Direct column (Si) | $H_2O$/butanol partition<br><br>Column (Si/ODS) | Direct column (Si) |
| Final Product | Oleanolic acid (g) | 0.63 | 1.3 | 0.14 |
|  | Purity (%) | 90.2 | 95.2 | 90.6 |
|  | Maslinic acid (g) | 0.11 | 4.1 | 0.02 |
|  | Purity (%) | 90.5 | 95.9 | 90.9 |

TABLE 1-continued

| | | Preparation Ex. No. | | | |
|---|---|---|---|---|---|
| | | 4 | 5 | 6 | 7 |
| Raw Material | | Extraction residues | | | |
| Extraction solvent | | $H_2O$—EtOH[1)] | | | |
| Ext. product | Amt. of Ext. (g) | 41 | 41 | 41 | 65.6 |
| | Content of oleanolic acid (%) | 3.2 | 3.1 | 3.1 | 3.1 |
| | Content of maslinic acid (%) | 11.0 | 11.0 | 11.0 | 10.5 |
| Concentration/ Fractionation | | $H_2O$/ butanol | *) | **) | **) |
| Purification | | Column (Si/ODS) | Column (Si) | Column (Si/ODS) Recrystallization | Column (Si/ODS) |
| Final Product | Oleanolic acid (g) | 1.3 | 6.2 ***) | 1.1 | 2.0 |
| | Purity (%) | 96.0 | 88.6 ***) | 99.0 | 99.1 |
| | Maslinic acid (g) | 4.5 | — | 3.7 | 6.6 |
| | Purity (%) | 96.3 | — | 99.1 | 99.2 |

[1)] $H_2O$—EtOH: Water-containing ethanol.
*) After evaporation to dryness, water-insoluble matter is recovered.
**) After the removal of ethanol, water-insoluble matter is recovered.
***) The sum of oleanolic acid and maslinic acid.

The results obtained in Preparation Examples 1 to 7 clearly indicate that the method of the present invention permits the preparation of highly purified olcanolic acid and maslinic acid and that the method is also excellent from the viewpoint of the yields thereof.

First, when comparing the total contents of oleanolic acid and maslinic acid present in the extracted products with one another, it is proved that the extraction with the water-containing ethanol as a hydrophilic solvent is superior to the extraction with hexane as a hydrophobic solvent. It is found that in case where it is intended to obtain, in particular, maslinic acid, the extraction with the water-containing ethanol as a hydrophilic solvent is rather effective.

In addition, when comparing the contents of oleanolic acid and maslinic acid in the products extracted with water-containing ethanol with one another, it is found that the content in the extracted product derived from extraction residue is higher than that observed for the product derived from compressed residue. Although compressed residues may provide an extracted product having a high content of oleanolic acid and/or maslinic acid, the extracted product derived from extraction residue would permit the more efficient concentration and/or fractionation-purification of oleanolic acid and/or maslinic acid since the extracted product derived from extraction residue has a smaller content of contaminants such as oily components and therefore, the extraction residue is rather excellent as a raw material used herein.

Moreover, as to the concentration process, the target compounds can be concentrated by the general and simple method such as the liquid—liquid partition technique using a solvent, but the target compounds may likewise easily be concentrated by a quite simple method such as the recovery of water-insoluble matters from the extracted product. This recovery of water-insoluble matters may be applied to a simple aqueous system to concentrate the same without using any solvent and therefore, this is a quite excellent method even from the viewpoint of handling ability and safety. It is also clear that quite high pure oleanolic acid and maslinic acid can be prepared by the use of a general purification technique such as the fractionation by column chromatography and recrystallization.

As has been discussed above in detail, the preparation method of the present invention is one permitting the preparation of highly purified oleanolic acid and maslinic acid from olive plant in a high yield. Accordingly, the method of the present invention is considered to be an industrially quite efficient method for preparing oleanolic acid and maslinic acid.

According to the present invention, oleanolic acid and/or maslinic acid and physiologically acceptable salts thereof can suitably be obtained from olive plant and/or products generated in the olive oil-manufacturing processes. In other words, the method is one permitting the preparation of oleanolic acid and/or maslinic acid and physiologically acceptable salts thereof in high yields. Further these compounds can be prepared from products generated in the olive oil-manufacturing processes and therefore, the method of the invention permits the preparation of these compounds in quite low production cost.

What is claimed is:

1. A method for preparing oleanolic acid, maslinic acid, a mixture of oleanolic and maslinic acid, or physiologically acceptable salts thereof comprising the steps of:
    extracting an olive plant, products obtained in an olive oil-manufacturing process, or mixtures thereof, with water, a hydrophilic organic solvent or mixtures thereof, and then
    concentrating the resulting extract.

2. The method of claim 1 wherein it further comprises the step of:
    treating the resulting extracted substance or extracted liquid with an acidic medium, an acidic substance, or both the acidic medium and the acidic substance.

3. The method of claim 1 wherein it further comprises the step of:
    treating the resulting extracted substance or liquid extract with a basic medium, a basic substance, or both the basic medium and the basic substance.

4. The method of claim 1, wherein the olive plant comprises at least one member selected from the group consisting of fruits, seeds, rinds, leaves, stems and buds or germs of olive and dried products, pulverized products and defatted products of these ingredients.

5. The method of claim 1, wherein the products obtained in the olive oil-manufacturing process comprise at least one member selected from the group consisting of compressed residues, extraction residues, squeezed oil, extracted oil, degummed oil scum, deacidified oil scum, dark oil, waste decoloring agent, deodorized scum, oil-expressed juice, waste water and waste filter mediums.

6. The method of claim 1, wherein the hydrophilic organic solvent is at least one member selected from the group consisting of alcohols, mixtures of chloroform and alcohols, acetone, tetrahydrofuran, dimethylsulfoxide and pyridine.

7. The method of claim 1, wherein the hydrophilic organic solvent is at least one member selected from the group consisting of (1) a mixed solvent comprising chloroform and methanol; chloroform and ethanol; or chloroform, methanol and ethanol, (2) pyridine, (3) ethanol, (4) dimethylsulfoxide and (5) ethyl acetate.

8. The method of claim 1, wherein the products obtained in the olive oil-manufacturing process are compressed residues or extraction residues and the organic solvent is a water-containing alcohol.

9. The method of claim 8, wherein the products obtained in the olive oil-manufacturing process are extraction residues.

10. The method of claim 8, wherein the water-containing alcohol has an alcohol content ranging from 10 to 95% by mass and the alcohol is one having 1 to 4 carbon atoms.

11. The method of claim 1, wherein the extraction is conducted using water, a hydrophilic organic solvent or mixtures thereof, having a temperature of not less than 50° C.

12. The method of claim 1, wherein the extraction is conducted under pressure.

13. The method of claim 1, wherein the concentration step is at least one treatment selected from the group consisting of soluble contents recovering treatment, insoluble contents recovering treatment or both the soluble and insoluble contents recovering treatments, which make use of the solubility of the components present in the extract in water, organic solvent or mixtures thereof; liquid—liquid partition using water-hydrophobic organic solvent systems; recrystallization; re-precipitation; and a treatment, in which precipitates formed through cooling are recovered.

14. The method of claim 1, wherein the total content of oleanolic acid, maslinic acid and physiologically acceptable salts thereof, present in a mixture comprising oleanolic acid, maslinic acid and physiologically acceptable salts thereof, prepared according to the method as set forth in claim 1, ranges from 85% to 100%.

15. The method of claim 1, wherein the total content of oleanolic acid and physiologically acceptable salts thereof in a mixture comprising oleanolic acid and physiologically acceptable salts thereof, prepared according to the method as set forth in claim 1, is not less than 90%.

16. The method of claim 1, wherein the total content of maslinic acid and physiologically acceptable salts thereof in a mixture comprising maslinic acid and physiologically acceptable salts thereof, prepared according to the method as set forth in claim 1, is not less than 90%.

17. A method for preparing olcanolic acid, maslinic acid, a mixture of oleanolic and maslinic acid, or physiologically acceptable salts thereof comprising the steps of:

extracting an olive plant, products obtained in an olive oil-manufacturing process, or mixtures thereof, with water, a hydrophilic organic solvent or mixtures thereof, and then conducting a fractionation-purification treatment of the resulting extract.

18. The method of claim 17, wherein the fractionation-purification treatment is at least one member selected from the group consisting of recrystallization, re-precipitation, purification by normal phase chromatography, purification by reversed phase chromatography, purification by normal phase and reversed phase chromatography, decolorization and deodorization.

19. The method of claim 17, wherein the total content of oleanolic acid, maslinic acid and physiologically acceptable salts thereof, present in a mixture comprising oleanolic acid, maslinic acid and physiologically acceptable salts thereof, prepared according to the method as set forth in claim 21, ranges from 85% to 100%.

20. The method of claim 17, wherein the total content of oleanolic acid and physiologically acceptable salts thereof in a mixture comprising olcanolic acid and physiologically acceptable salts thereof, prepared according to the method as set forth in claim 21, is not less than 90%.

21. The method of claim 17, wherein the total content of maslinic acid and physiologically acceptable salts thereof in a mixture comprising maslinic acid and physiologically acceptable salts thereof, prepared according to the method as set forth in claim 21, is not less than 90%.

22. A method for preparing oleanolic acid, maslinic acid, a mixture of oleanolic and maslinic acid, or physiologically acceptable salts thereof comprising the steps of:

extracting an olive plant, products obtained in an olive oil-manufacturing process, or mixtures thereof, with water, a hydrophilic organic solvent or mixtures thereof, and then concentrating and conducting a fractionation-purification treatment, of the resulting extract.

23. The method of claim 22, wherein the fractionation-purification treatment is at least one member selected from the group consisting of recrystallization, re-precipitation, purification by normal phase chromatography, purification by reversed phase chromatography, purification by normal and reversed phase chromatography, decolorization and deodorization.

24. The method of claim 22, wherein the total content of olcanolic acid, maslinic acid and physiologically acceptable salts thereof present in a mixture comprising oleanolic acid, maslinic acid and physiologically acceptable salts thereof, prepared according to the method as set forth in claim 26, ranges from 85% to 100%.

25. The method of claim 22, wherein the total content of oleanolic acid and physiologically acceptable salts thereof in a mixture comprising oleanolic acid and physiologically acceptable salts thereof, prepared according to the method as set forth in claim 26, is not less than 90%.

26. The method of claim 22, wherein the total content of maslinic acid and physiologically acceptable salts thereof in a mixture comprising maslinic acid and physiologically acceptable salts thereof, prepared according to the method as set forth in claim 26, is not less than 90%.

* * * * *